US009060682B2

(12) United States Patent
Lokshin

(10) Patent No.: US 9,060,682 B2
(45) Date of Patent: Jun. 23, 2015

(54) DISTRIBUTED SYSTEMS AND METHODS TO MEASURE AND PROCESS SPORT MOTIONS

(71) Applicant: AlpineReplay, Inc., Huntington Beach, CA (US)

(72) Inventor: David J. Lokshin, Huntington Beach, CA (US)

(73) Assignee: AlpineReplay, Inc., Huntington Beach, CA (US)

( * ) Notice: Subject to any disclaimer, the term of this patent is extended or adjusted under 35 U.S.C. 154(b) by 146 days.

(21) Appl. No.: 13/660,265

(22) Filed: Oct. 25, 2012

(65) Prior Publication Data

US 2014/0120838 A1    May 1, 2014

(51) Int. Cl.
| | | |
|---|---|---|
| *H04B 7/00* | (2006.01) | |
| *A61B 5/00* | (2006.01) | |
| *A61B 5/11* | (2006.01) | |
| *A63B 24/00* | (2006.01) | |

(52) U.S. Cl.
CPC .............. *A61B 5/0022* (2013.01); *A61B 5/1112* (2013.01); *A63B 24/0062* (2013.01); *A61B 2503/10* (2013.01)

(58) Field of Classification Search
CPC .. H04L 67/12; H04W 84/18; H04M 2250/02; H04M 2250/04
USPC ....................... 455/66.1, 41.2, 41.3
See application file for complete search history.

(56) References Cited

U.S. PATENT DOCUMENTS

| | | |
|---|---|---|
| 5,297,050 A | 3/1994 | Ichimura et al. |
| 5,345,382 A | 9/1994 | Kao |
| 5,452,869 A | 9/1995 | Basuthakur |
| 5,562,266 A | 10/1996 | Achkar |
| 5,636,146 A | 6/1997 | Flentov |
| 5,724,265 A | 3/1998 | Hutchings |
| 5,813,990 A | 9/1998 | Ryll |
| 5,960,380 A | 9/1999 | Flentov |
| 5,991,692 A | 11/1999 | Spencer, II |
| 6,266,623 B1 | 7/2001 | Vock |
| 6,496,787 B1 | 12/2002 | Flentov |
| 6,499,000 B2 | 12/2002 | Flentov |
| 6,539,336 B1 | 3/2003 | Vock |
| 6,729,176 B2 | 5/2004 | Begin |
| 6,813,586 B1 | 11/2004 | Vock et al. |
| 6,856,934 B2 | 2/2005 | Vock |
| 6,885,971 B2 | 4/2005 | Vock |
| 6,959,259 B2 | 10/2005 | Vock |

(Continued)

OTHER PUBLICATIONS

International Patent Application PCT/US2012/071867, International Search Report and Written Opinion, Jul. 4, 2013.

(Continued)

*Primary Examiner* — Lewis West
(74) *Attorney, Agent, or Firm* — Greenberg Traurig LLP

(57) ABSTRACT

A distributed, multi-stage, intelligent system is configured to determine user action performance characteristics parameters in action sports. Ruggedness, complexity, and cost are unevenly distributed among components across the stages for improved overall performance and reduced cost. The system includes stage-one, wearable devices configured to use sensors to collect initial data and transfer the initial data to stage-two devices which may temporally store the initial data and/or perform further data processing to generate intermediate data for communication to one or more stage-three devices configured for long term data storage, further processing and presentation.

21 Claims, 4 Drawing Sheets

(56) References Cited

U.S. PATENT DOCUMENTS

| | | |
|---|---|---|
| 7,054,784 B2 | 5/2006 | Flentov |
| 7,072,789 B2 | 7/2006 | Vock |
| 7,162,392 B2 | 1/2007 | Vock |
| 7,379,842 B2 | 5/2008 | Alexander |
| 7,386,401 B2 | 6/2008 | Vock |
| 7,393,422 B2 | 7/2008 | Nagao |
| 7,451,056 B2 | 11/2008 | Flentov |
| 7,512,515 B2 | 3/2009 | Vock |
| 7,628,074 B2 | 12/2009 | Vannucci |
| 7,640,135 B2 | 12/2009 | Vock |
| 7,657,183 B2 | 2/2010 | Drago |
| 7,667,645 B2 | 2/2010 | Tekawy |
| 7,715,982 B2 | 5/2010 | Grenfell et al. |
| 7,860,666 B2 | 12/2010 | Vock |
| 7,991,565 B2 | 8/2011 | Vock |
| 8,036,826 B2 | 10/2011 | MacIntosh et al. |
| 2003/0137433 A1 | 7/2003 | Schiller et al. |
| 2006/0247504 A1 | 11/2006 | Tice |
| 2007/0027367 A1 | 2/2007 | Oliver et al. |
| 2007/0055468 A1 | 3/2007 | Pylvanainen |
| 2007/0063850 A1 | 3/2007 | Devaul et al. |
| 2009/0070056 A1 | 3/2009 | Vocali |
| 2010/0204615 A1 | 8/2010 | Kyle et al. |
| 2011/0313731 A1 | 12/2011 | Vock et al. |
| 2012/0004883 A1 | 1/2012 | Vock |

OTHER PUBLICATIONS

Valerie Pitt, The Penguin Dictionary of Physics, 1977, Penguin, Harmondsworth, New York.

International Patent Application Serial No. PCT/US2011/059825, International Search Report and Written Opinion, Jun. 1, 2012.

DISTRIBUTED SYSTEMS AND METHODS TO MEASURE AND PROCESS SPORT MOTIONS

FIELD OF THE TECHNOLOGY

At least some embodiments of the present disclosure relate to measurements of motion parameters, such as the performance of an action during action sports.

BACKGROUND

Action sports may involve extreme motions with high speed, acceleration, and extreme forces. When actions take place at different time or at different locations, it can be difficult to objectively compare the achievements of different participants.

A wide spread of microprocessors, inertial sensors and Global Positioning System (GPS) devices allows to accurately measure such motions, quantifying them in term of speed, acceleration, air time, rotation, flip, etc., and then compare these data independent on where and when the action was performed.

There are multiple systems that address such measurements. However, existing systems typically use a single wearable device which combines sensors, GPS receiver, memory and processing power sufficient to perform sensor measurement and computation of the performance characteristics. In some cases, results are wirelessly sent to a remote location for storage and display.

Such systems have some significant limitations. For example, due to the fast and complicated nature of the action sport motion, the computational and algorithmic complexity in the determination of the performance characteristics can be very significant. In addition, to compare performance between different sportsmen, different venues, and different time, the performance data is stored in a common searchable database. A common way used in the existing systems is to transfer data to a database is based on a wireless communication which farther increases complexity and cost of the wearable device.

Further, due to the nature of the action sports, such as high altitude mountain ski, wake boarding, windsurfing, etc., it is desirable that the devices used to collect data are very rugged and highly reliable, which is difficult to achieve in a highly complicated, multi-function wearable device.

Further, very often there is no reliable high speed data connection at the locations where the action sports are performed to facilitate the transfer of data to the common searchable database.

BRIEF DESCRIPTION OF THE DRAWINGS

The embodiments are illustrated by way of example and not limitation in the figures of the accompanying drawings in which like references indicate similar elements.

DETAILED DESCRIPTION

The following description and drawings are illustrative and are not to be construed as limiting. Numerous specific details are described to provide a thorough understanding. However, in certain instances, well known or conventional details are not described in order to avoid obscuring the description. References to one or an embodiment in the present disclosure are not necessarily references to the same embodiment; and, such references mean at least one.

At least one embodiment of the present disclosure provides systems and methods for the measuring, monitoring, and/or processing sport motions in a way that is very reliable, environmentally rugged, with reduced cost, and improved operation reliability without loss of data in the extreme environment even when there is no reliable wireless connectivity to a wide area network.

In one embodiment, a distributed, multi-stage, intelligent system is configured to unevenly distribute ruggedness, complexity, and cost among multiple components for improved overall performance. In one embodiment, the system includes stage-one, wearable devices configured to use sensors to collect initial data and transfer initial data to stage-two devices which may temporally store the initial data and/or perform further data processing to generate intermediate data for communication to one or more stage-three devices configured for long term data storage, further processing and presentation.

In one embodiment, the power usage and algorithmic complexity of the devices of different stages increase when the data flows from the low stage devices for sensor data generation to high stage devices for processing, storage and/or presentation. Ruggedness of the devices decreases from devices for data capture to devices for processing, storage and presentation of multi-user performance characteristics parameters.

Figure 3:
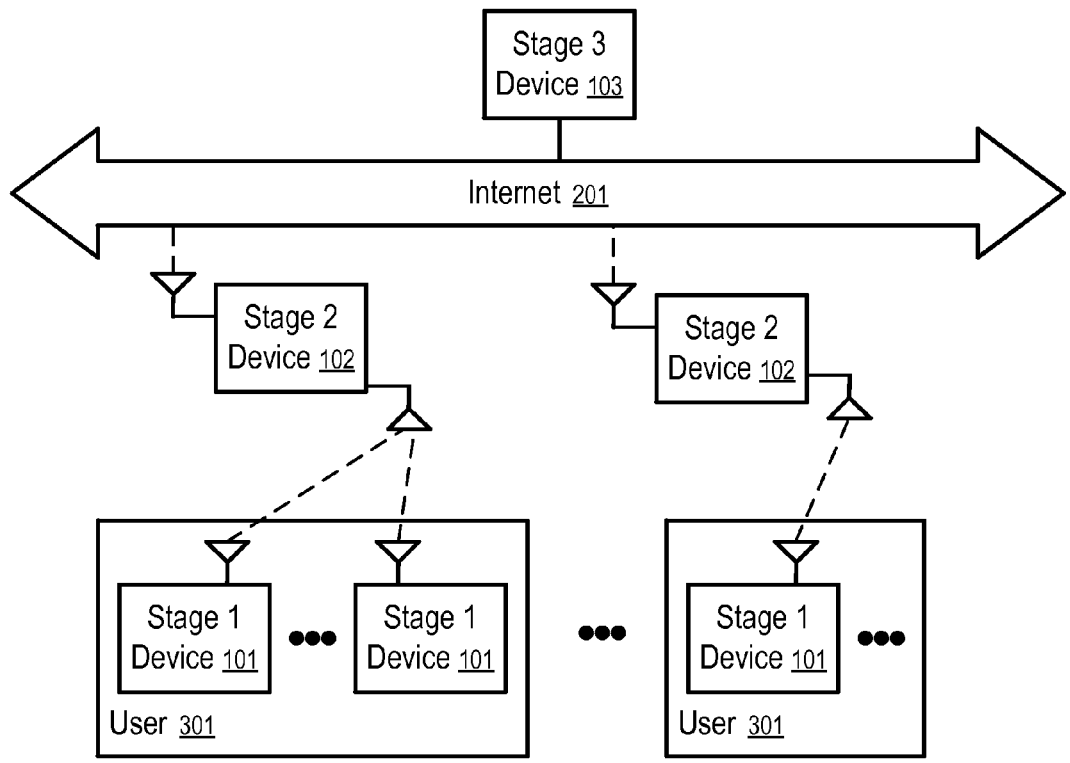
FIG. 3 shows a distributed, multi-stage, intelligent system to measure sport motion parameters according to one embodiment.

FIG. 3 shows a distributed, multi-stage, intelligent system configured to collect, process, store and transfer data related to sport motion measurements according to one embodiment.

In one embodiment, a user (301) may have one or more stage-one devices (101) attached to the body and/or equipment of the user and one stage-two device (102) associated with the user (301). A single stage-two device (102) is sufficient to operate with a plurality of stage-one devices (101) attached to the user (301). However, the user (301) may optionally choose to use more than one stage-two devices (101) to concurrently operate with separate groups of stage-one devices (101) attached to the user (301). Multiple stage-two devices (102) associated with multiple respective users (301) are connected to the same stage-three device (103).

In FIG. 3, sensor data are collected on stage-one devices (101) that are configured to be attached directly to a user (301). For example, the stage-one devices (101) can be placed on the sport equipment used by the user (301), on the cloth or arm band of the user (301), in the pocket of the user (301), or any other way that is directly connected to the user (301).

The stage-one devices (101) attached to a user (301) are configured to transfer data, via low power, low range wireless communication link to a stage-two device (102) wearable by the user (301) as well. The stage-two device (102) performs data pre-processing and sends packaged data via a long range wireless communication link (e.g., via the Internet) to a stage-three device (103) which performs the complex computations and provides database functions.

Figure 1:
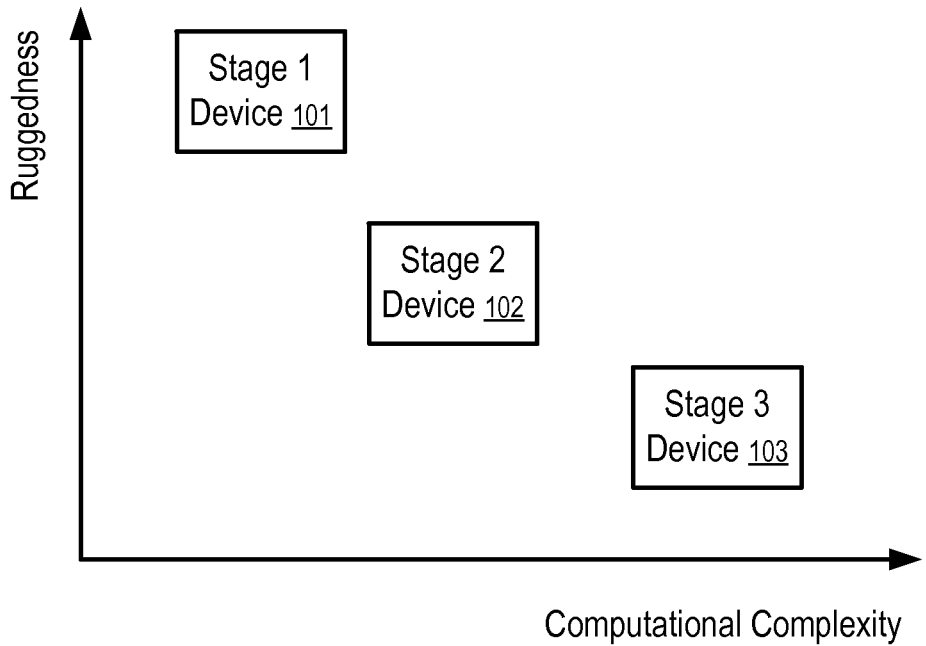
FIG. 1 illustrates a distribution of computational complexity and ruggedness of devices according to one embodiment.
Figure 2:
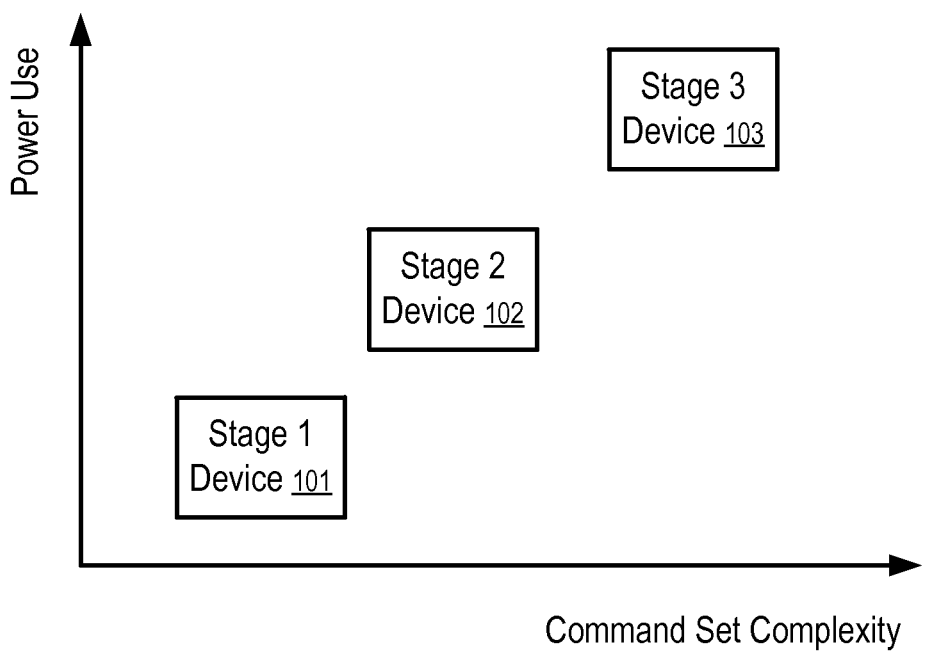
FIG. 2 illustrates a distribution of command set complexity and power use level of devices according to one embodiment.

FIGS. 1 and 2 illustrate relations between ruggedness, power use, and complexity between different processing stages.

In FIG. 1, the ruggedness of stage-one devices (101) is higher than the ruggedness of stage-two devices (102), while the computational complexity of stage-one devices (101) is lower than the computational complexity of stage-two devices (102). The ruggedness of stage-two devices (102) is higher than the ruggedness of stage-three devices (103), while the computational complexity of stage-two devices (102) is lower than the computational complexity of stage-three devices (103).

In FIG. 2, the power use of stage-one devices (101) is lower than the power use of stage-two devices (102), while the command set complexity of stage-one devices (101) is also lower than the command set complexity of stage-two devices (102). The power use of stage-two devices (102) is lower than the power use of stage-three devices (103), while the command set complexity of stage-two devices (102) is also lower than the command set complexity of stage-three devices (103).

Figure 4:
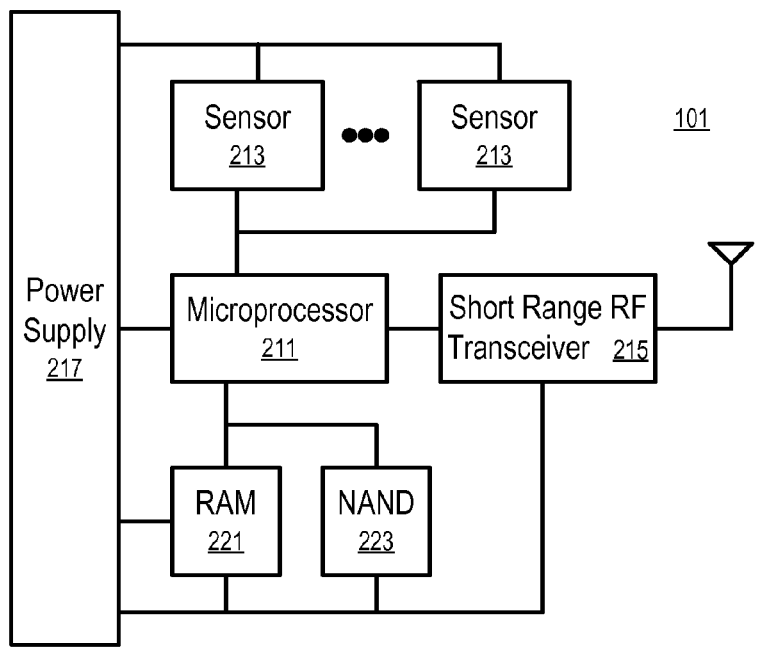
FIG. 4 shows a stage-one device according to one embodiment.

FIG. 4 shows a stage-one device according to one embodiment. In FIG. 4, the stage-one sensor device (101) is the most rugged, most reliable, most power efficient device among the devices of different stages, but the least complicated and least algorithmically sophisticated and is limited to a short range of wireless communication (e.g., via wireless personal area network communication connection to a stage-two device (102)).

In one embodiment, the stage-one sensor device (101) is configured to reliably collect sensor data in the environment of extreme sports with minimum power usage and minimum or no data loss.

In FIG. 4, the stage-one device (101) includes sensors (213) to collect various sensor data, such as GPS data collected at a given sampling rate (e.g., 5 Hz) for position/velocity determination and/or time data, magnetic inclination data (e.g., angle between Earth magnetic vector and vertical) collected at a given sampling rate (e.g., 15 Hz), accelerometer data collected at a given sampling rate (e.g., 50 Hz), gyro sensor data for rotation determination collected at a given sampling rate (e.g., 100 Hz), etc.

In one embodiment, the microprocessor (211) of the stage-one device (101) is limited in computational capability, when compared with the computational capability of the microprocessor (211) of the stage-two device (102) or the stage-three device (103).

In one embodiment, the stage-one device (101) is configured to optimize data collection.

For example, in one embodiment, the stage one device (101) is configured to change from collecting data at a low sampling rate to collecting data at a high sampling rate when the microprocessor (211) of the stage one device (101) determines that such a high sampling rate is desirable based on a preliminary analysis of data collected at the low frequency sampling rate. For example, in one embodiment, the stage one device (101) is configured to collect accelerometer and gyro data when the current velocity as determined from GPS data is above a predetermined threshold and not to collect the accelerometer and gyro data when the current velocity as determined from GPS data is below a predetermined threshold.

In one embodiment, the stage-one device (101) is configured to perform initial data conditioning such as sensor calibration, individual and cross calibration, temperature reference, temperature compensation, etc.

In one embodiment, the stage-one device (101) supports a limited set of commands that it can recognize and collects the data into its internal memory (e.g., RAM 221 and/or nonvolatile, flash memory 223) to prevent data loss.

In one embodiment, the stage-one device (101) is configured to performs sensor measurements using one or more sensors (213), stores measurement data in its internal memory (e.g., 221 and 223), sends the measurement data to a stage-two device (102) on request from the stage-two device using the short range radio frequency (RF) transceiver (215) via low power short range wireless communication.

In one embodiment, a stage-one device is configured as a dedicated rugged sensor device having a power supply (217).

Figure 5:
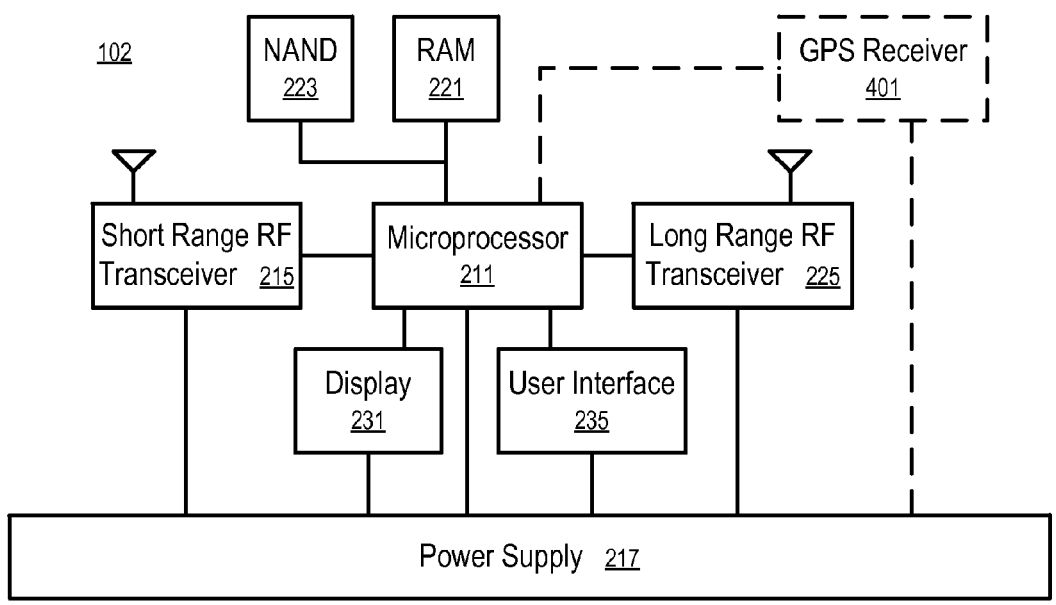
FIG. 5 shows a stage-two device according to one embodiment.

FIG. 5 shows a stage-two device according to one embodiment.

In one embodiment, the stage-two device (102) is configured to collect data from stage-one devices and communicate with a remotely located central server (e.g., a stage-three device (103)) via long range wireless communication using a long range radio frequency (RF) transceiver (225).

In one embodiment, the stage-two device (103) is configured to command stage-one devices (101) and collect data from stage-one devices (101) using a short range RF transceiver (215) (e.g., through a wireless personal area network), send combined data to the stage-three device(s) (103) via a long range RF transceiver (215) (e.g., through wireless local area network, or wireless wide area network).

In one embodiment, the stage-two device (102) is configured to receive instructions and information from stage-three devices (103) and pass the instructions to stage-one devices (101).

In one embodiment, when requested the stage-two device (102) is configured to download new firmware into the memory (e.g., flash memory 223) of stage-one devices (103) to update and/or calibrate the stage-one devices (103).

In one embodiment, the stage-two device (102) is configured to provide user interface (235) to receive input from the user (301) and present information on the display device (231) (or an audio device).

In one embodiment, the microprocessor (211) of the stage-two device (102) is configured (e.g., via instructions stored in the memory (e.g., 221, 223) to collect data from a set of stage-one devices (101), pre-process the data (e.g., to reduce the amount of data to be transferred to the stage-three device (103)), and to send the processed data to the stage-three device (103). The stage-two device (102) has both low power, short range communication capability and long range, high power communication capability.

In one embodiment, a stage-two device (102) is configured as a master of a set of a stage-one devices (103) associated with a user (301) to whom the stage-one devices (103) are attached. For example, a first dedicated stage-one device (103) is configured as a sensor device mounted on the snowboard of the user (301), while a second stage-one device (103) is configured with a sensor set embedded in a camera mounted on a helmet of the user (301).

Using the short range RF transceiver (215), the stage-two device (215) is configured to command the stage-one devices (101) to start/stop data collection, sets the operating parameters of the stage-one devices (101), such as sampling rate, signal conditioning parameters, etc.

In one embodiment, the stage-two device (215) is configured to perform preliminary data processing of the measurements to determine, for the user (301), performance parameters such as maximum speed, total distance, etc. The determined measurements can be presented on the display (231) of the stage-two device (215).

In one embodiment, the user interface (235) of the stage-two device (102) is configured to receive from the user (301) instructions to start/stop data collection, and initiate data transfer.

Using the long range RF transceiver (225), the stage-two device (102) is configured to receive instructions, data, and/or information from a stage-three device (103). The received instructions, data and/or information are processed and then sent to the stage-one devices (101) or displayed to the user (301) via the display (231).

Since the stage-two device (102) is not required to be as rugged as the stage-one device (103), the overall system cost and complexity is reduced. Further, the functions of the stage-two device (102) are shared among a plurality of stage-one devices (101), the cost of the overall system is reduced.

In one embodiment, a stage-two device (102) is implemented as a cell phone with low power Bluetooth transceiver as the short range RF transceiver (215) and a 3G/4G cellular or Wi-Fi communication transceiver as the long range RF transceiver (225). Alternatively, a stage-two device (102) is configured as a dedicated base station capable of low power short range communication with stage-one devices (101), and Wi-Fi or wired communication with a personal computer.

In one embodiment, the stage-two device (102) includes an optional GPS receiver (401). When equipped with the GPS receiver (401), the stage-two (102) is configured to instruct the stage-one devices (101) to start and/or stop data collection based on the motion parameters determined based on the measurement obtained via the GPS receiver (401) integrated within the stage-two device (102).

Figure 6:
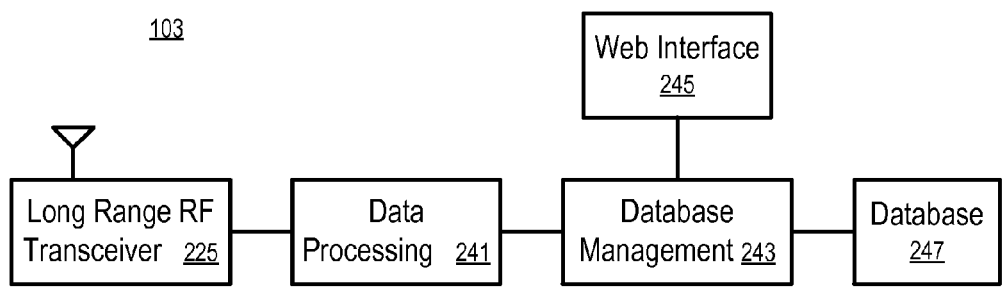
FIG. 6 shows a stage-three device according to one embodiment.

FIG. 6 shows a stage-three device according to one embodiment.

In one embodiment, a stage-three device (103) includes a server computer that communicates with a set of stage-two devices (102) via a predefined protocol over a network, such as Internet (201). The stage-three device (103) is configured to collect data from the stage-two devices (102) through the long range RF transceiver (225), perform data processing (241) of the data for each individual user (301) to compute detailed and accurate performance characteristics parameters based on the set of data received from the stage-two device (102) of the corresponding user (301), and perform database management (243) to store the computed performance characteristics parameters into a database (247) configured for the particular sport.

In one embodiment, the stage-three device (103) is configured to use long range RF transceiver (225) to communicate with stage-two devices (102) over wide band communication channel such as Internet. The stage-three device (103) may use a wireless telecommunications network, such as cellular communications network, to communicate with the stage-two devices (102). Alternatively, the stage-three device (103) is configured to be connected to the stage-two devices (102) via a wired network connection.

In one embodiment, the stage-three device (103) is configured to perform time synchronization of multiple sensor data received, via stage-two devices (102), from the stage-one devices (101).

In one embodiment, the stage-three device (103) is configured to perform time synchronization between data received from stage-one and stage-two devices (101 and 102).

In one embodiment, the stage-three device (103) is configured to perform computation of various sportsman performance parameters such as speed, air time, jump height, calories burned, etc., based on the data received from the stage-one and stage-two devices (101 and 102).

In one embodiment, the stage-three device (103) is configured to send computed performance parameters and their ranking to the stage-two devices (102) for user viewing. In one embodiment, the stage-three device (103) includes a web interface (245) configured to allow a user (301) and/or other persons to access the performance data stored in the database (247).

In one embodiment, the stage-three device (103) is configured to perform sensors cross correlation based on the received data, and sending, via the stage-two devices (102), back to the stage-one devices (101) the parameters for calibration procedures.

In one embodiment, the stage-three device (103) is configured to perform database management (243) of the user performance parameters.

In one embodiment, the stage-three device (103) is connected to the Internet for communications with the stage-two devices (102).

In one embodiment, each of the stage-one devices (101) and the stage-two devices (102) are disposed within a separate housing and configured to be attached separately to the body of the user (301) via clothing, sporting equipment, band, helmet, etc.

The multi-stage, distributed system disclosed herein has complexity increases at stages from sensor data collection to performance parameter determination and storage at a central location, while ruggedness and power requirements decrease. The system allows creating a sophisticated but efficient sport performance monitoring system capable of serving action sport enthusiasts in harsh environment with low cost, low power, high performance, and high reliability.

The systems and methods of the present disclosure overcome various limitations in the conventional systems.

In a conventional system, the overall device cost is high, since various functions related to sensors, GPS receivers, memory and processing power for sensor measurement and computation of the performance characteristics are implemented in a single wearable device. If several sensors need to be connected to a sportsman, the overall cost may grow significantly.

In the conventional system, the single device is configured to perform multiple different functions, such as sensor measurement at a high sampling rate, complicated and fast data processing, display, user interface, wireless communication, etc. Such operations are power hungry and require significant power source that may be too large to be easily wearable by the sportsman.

In the distributed system of the present disclosure, the functions implemented in the stage-one devices are reduced. Multiple stage-one devices (101) can rely upon one stage-two device (102) to provide the functions implemented in the stage-two device (102). Thus, the overall cost of one user using separate sensor devices is reduced.

Since the stage-one devices are used to implement reduced functions, the stage-one devices can be implemented to be very small and rugged for use in extreme sports.

In the conventional system, the data processing algorithms implemented in sensor devices are complicated and need to be constantly improved and updated. With thousands of devices in the field it could be difficult to ensure that all the devices use the same data processing algorithm and therefore, compete under the same conditions.

In the distributed system of the present disclosure, the complex computation of the performance characteristic parameters is performed at the stage-three device (103). Thus, the same computation process can be applied to sensor data of different users (301).

In the conventional system, multiple sensors are attached to the multiple locations at the sportsman and his equipment. Since each sensor device computes based its own measurements, the conventional system does not have the capability to combine sensor data from different sensor devices to take advantage of the multi-relation between the different sensors.

In the distributed system of the present disclosure, a stage-two device (102) and/or the stage-three device (103) can be configured to take advantage of multi-relation between the different sensors devices in communication with the stage-two device (102).

Thus, the systems and methods of the present disclosure is highly reliable, low cost, high performance, and allows to record, analyze, transmit, and store individual performance data even in the harshest environment.

Figure 7:
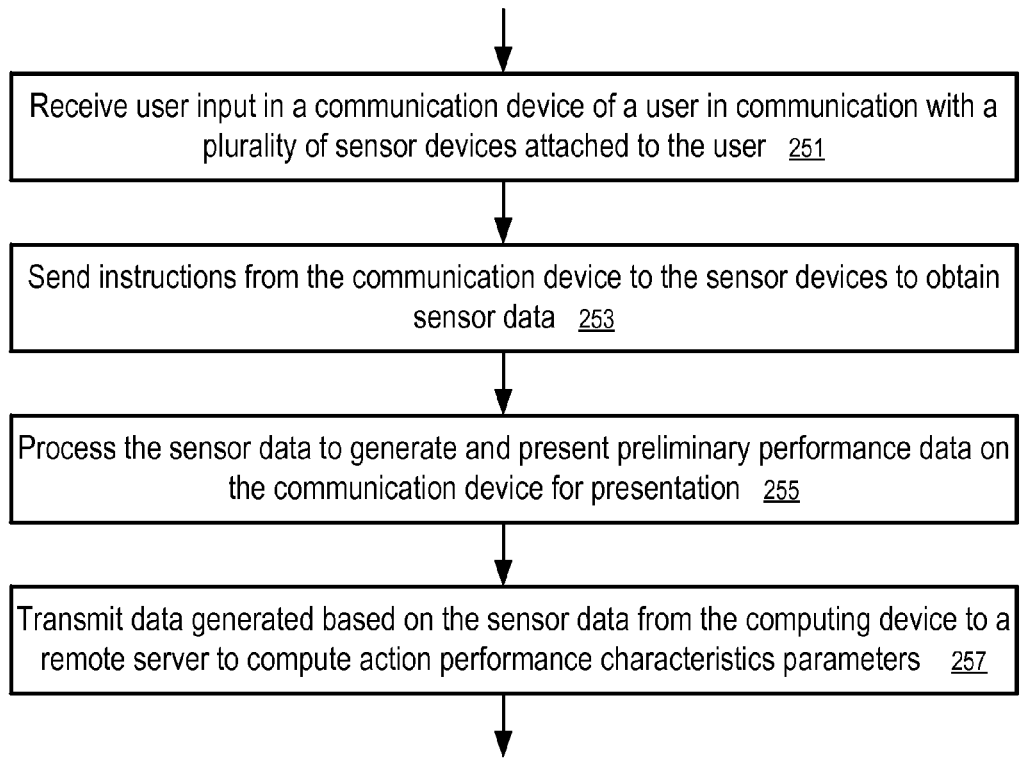
FIG. 7 shows a method to measure motion parameters according to one embodiment.

FIG. 7 shows a method to measure motion parameters according to one embodiment. In FIG. 7, a communication device (e.g., a stage-two device (102)) of a user (301) is configured to receive (251) user input via a user interface (235). The communication device (e.g., 102) is configured to be in communication, via short range wireless communication links (e.g., wireless personal area network), with a plurality of sensor devices (e.g., stage-one devices (101)) attached to the user (301). Each of the communication device and the sensor devices is in a housing separate from others. The communication device (e.g., 102) is configured to send (253) instructions, in response to the user input, to the sensor devices (e.g., 101) to obtain sensor data during the user (301) performing a sport action. The communication device (e.g., 102) is configured to process (255) sensor data received from the sensor devices (e.g., 101) and present preliminary performance data on the communication device (e.g., 102) for presentation using the user interface (235) of the communication device (e.g., 102). The communication device (e.g., 102) is configured to transmit data generated based on the sensor data received from the sensor devices (e.g., 101) to a remote server (e.g., a stage-three device (103)). The remote server (e.g., 103) is configured to compute (257) action performance characteristic parameters using the data transmitted from the communication device (e.g., 102).

In one embodiment, the communication device (e.g., 102) is configured to use multi-relation among sensor data received from different sensor devices (e.g., 101) to generate the preliminary performance data.

In one embodiment, the remote server (e.g., 103) is configured to compute the action performance characteristic parameters based on multi-relation among sensor data received from different sensor devices (e.g., 101) to generate the preliminary performance data.

In one embodiment, the sensor devices (e.g., 101) are configured without user interfaces to show information based on the sensor data.

Figure 8:
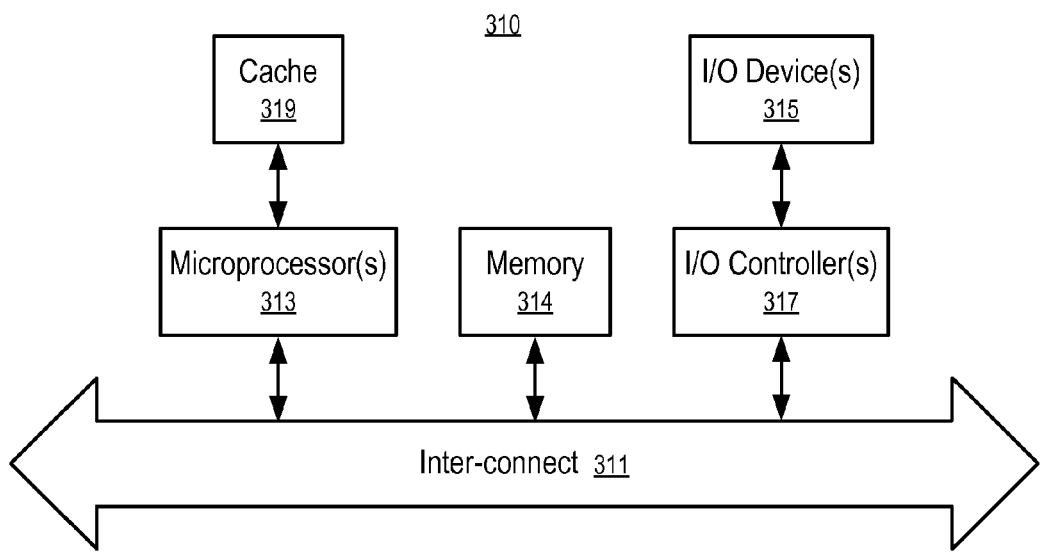
FIG. 8 shows a data processing system according to one embodiment.

In one embodiment, at least some of the devices, such as the stage-two device (102), the stage-three device (103), can be implemented using one or more data processing systems as illustrated in FIG. 8, with more or less components.

FIG. 8 shows a data processing system according to one embodiment. While FIG. 8 illustrates various parts of a computer system, it is not intended to represent any particular architecture or manner of interconnecting the parts. One embodiment may use other systems that have fewer or more components than those shown in FIG. 8.

In FIG. 8, the data processing system (310) includes an inter-connect (311) (e.g., bus and system core logic), which interconnects a microprocessor(s) (313) and memory (314). The microprocessor (313) is coupled to cache memory (319) in the example of FIG. 8.

In one embodiment, the inter-connect (311) interconnects the microprocessor(s) (313) and the memory (314) together and also interconnects them to input/output (I/O) device(s) (315) via I/O controller(s) (317). I/O devices (315) may include a display device and/or peripheral devices, such as mice, keyboards, modems, network interfaces, printers, scanners, video cameras and other devices known in the art. In one embodiment, when the data processing system is a server system, some of the I/O devices (315), such as printers, scanners, mice, and/or keyboards, are optional.

In one embodiment, the inter-connect (311) includes one or more buses connected to one another through various bridges, controllers and/or adapters. In one embodiment the I/O controllers (317) include a USB (Universal Serial Bus) adapter for controlling USB peripherals, and/or an IEEE-1394 bus adapter for controlling IEEE-1394 peripherals.

In one embodiment, the memory (314) includes one or more of: ROM (Read Only Memory), volatile RAM (Random Access Memory), and non-volatile memory, such as hard drive, flash memory, etc.

Volatile RAM is typically implemented as dynamic RAM (DRAM) which requires power continually in order to refresh or maintain the data in the memory. Non-volatile memory is typically a magnetic hard drive, a NAND flash memory, a magnetic optical drive, an optical drive (e.g., a DVD RAM), or other type of memory system which maintains data even after power is removed from the system. The non-volatile memory may also be a random access memory.

The non-volatile memory can be a local device coupled directly to the rest of the components in the data processing system. A non-volatile memory that is remote from the system, such as a network storage device coupled to the data processing system through a network interface such as a modem or Ethernet interface, can also be used.

In this description, some functions and operations are described as being performed by or caused by software code to simplify description. However, such expressions are also used to specify that the functions result from execution of the code/instructions by a processor, such as a microprocessor.

Alternatively, or in combination, the functions and operations as described here can be implemented using special purpose circuitry, with or without software instructions, such as using Application-Specific Integrated Circuit (ASIC) or Field-Programmable Gate Array (FPGA). Embodiments can be implemented using hardwired circuitry without software instructions, or in combination with software instructions. Thus, the techniques are limited neither to any specific combination of hardware circuitry and software, nor to any particular source for the instructions executed by the data processing system.

While one embodiment can be implemented in fully functioning computers and computer systems, various embodiments are capable of being distributed as a computing product in a variety of forms and are capable of being applied regardless of the particular type of machine or computer-readable media used to actually effect the distribution.

At least some aspects disclosed can be embodied, at least in part, in software. That is, the techniques may be carried out in a computer system or other data processing system in response to its processor, such as a microprocessor, executing sequences of instructions contained in a memory, such as ROM, NAND, volatile RAM, non-volatile memory, cache or a remote storage device.

Routines executed to implement the embodiments may be implemented as part of an operating system or a specific application, component, program, object, module or sequence of instructions referred to as "computer programs." The computer programs typically include one or more instructions set at various times in various memory and storage devices in a computer, and that, when read and executed by one or more processors in a computer, cause the computer to perform operations necessary to execute elements involving the various aspects.

A machine readable medium can be used to store software and data which when executed by a data processing system causes the system to perform various methods. The executable software and data may be stored in various places including for example ROM, NAND, volatile RAM, non-volatile memory and/or cache. Portions of this software and/or data may be stored in any one of these storage devices. Further, the data and instructions can be obtained from centralized servers or peer to peer networks. Different portions of the data and instructions can be obtained from different centralized servers and/or peer to peer networks at different times and in different communication sessions or in a same communication session. The data and instructions can be obtained in entirety prior to the execution of the applications. Alternatively, portions of the data and instructions can be obtained dynamically, just in time, when needed for execution. Thus, it is not required that the data and instructions be on a machine readable medium in entirety at a particular instance of time.

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., Compact Disk Read-Only Memory (CD ROMS), Digital Versatile Disks (DVDs), etc.), among others. The computer-readable media may store the instructions.

The instructions may also be embodied in digital and analog communication links for electrical, optical, acoustical or other forms of propagated signals, such as carrier waves, infrared signals, digital signals, etc. However, propagated signals, such as carrier waves, infrared signals, digital signals, etc. are not tangible machine readable medium and are not configured to store instructions.

In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

In various embodiments, hardwired circuitry may be used in combination with software instructions to implement the techniques. Thus, the techniques are neither limited to any specific combination of hardware circuitry and software nor to any particular source for the instructions executed by the data processing system.

The description and drawings are illustrative and are not to be construed as limiting. The present disclosure is illustrative of inventive features to enable a person skilled in the art to make and use the techniques. Various features, as described herein, should be used in compliance with all current and future rules, laws and regulations related to privacy, security, permission, consent, authorization, and others. Numerous specific details are described to provide a thorough understanding. However, in certain instances, well known or conventional details are not described in order to avoid obscuring the description. References to one or an embodiment in the present disclosure are not necessarily references to the same embodiment; and, such references mean at least one.

The use of headings herein is merely provided for ease of reference, and shall not be interpreted in any way to limit this disclosure or the following claims.

Reference to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, and are not necessarily all referring to separate or alternative embodiments mutually exclusive of other embodiments. Moreover, various features are described which may be exhibited by one embodiment and not by others. Similarly, various requirements are described which may be requirements for one embodiment but not for other embodiments. Unless excluded by explicit description and/or apparent incompatibility, any combination of various features described in this description is also included here. For example, the features described above in connection with "in one embodiment" or "in some embodiments" can be all optionally included in one implementation, except where the dependency of certain features on other features, as apparent from the description, may limit the options of excluding selected features from the implementation, and incompatibility of certain features with other features, as apparent from the description, may limit the options of including selected features together in the implementation.

In the foregoing specification, the disclosure has been described with reference to specific exemplary embodiments thereof. It will be evident that various modifications may be made thereto without departing from the broader spirit and scope as set forth in the following claims. The specification and drawings are, accordingly, to be regarded in an illustrative sense rather than a restrictive sense.

What is claimed is:

1. A system comprising:
a stage-one sensor device configured to be attached to a user during performance of sport actions, wherein the stage-one sensor device includes:
a processor;
a plurality of sensors coupled to the processor and configured to obtain measurements related to motions of the user in the sport actions;
a transceiver coupled to the processor for short range wireless communications; and
memory coupled to the processor and storing instructions that, when executed by the processor, cause the stage-one sensor device to:
collect sensor data from the plurality of sensors; and
transmit the sensor data via the transceiver;
a stage-two device that includes:
a processor;
a user interface coupled to the processor and configured to receive user instructions;
a first transceiver for short range wireless communications;
a second transceiver for long range wireless communications; and
memory coupled to the processor and storing instructions that, when executed by the processor, cause the second-stage device to:
receive the sensor data transmitted by the stage-one device via the first transceiver;
process the sensor data and present the processed sensor data via the user interface; and transmit the processed sensor data, using the second transceiver, to a server computing apparatus via a network, wherein the server computing apparatus is disposed at a location remote to the stage-one sensor device and the stage-two device, and the server computing apparatus is configured to time synchronize the processed sensor data from the plurality of sensors.

2. The system of claim 1, further comprising:
the server computing apparatus, comprising a database to store the input processed sensor data.

3. The system of claim 2, wherein the server computing apparatus is configured to generate action performance characteristics parameters based on the input data.

4. The system of claim 3, wherein the action performance characteristics parameters include at least one of: speed, distance, vertical drop, air time, jump height, and jump rotation.

5. The system of claim 2, wherein the server computing apparatus further comprises a web interface to present rankings of users based on the processed sensor data.

6. The system of claim 1, wherein, wherein the plurality of sensors of the stage-one sensor device include at least one of:
a Global Positioning System receiver;
a rotation sensor;
an accelerometer; and
a magnetic inclination sensor.

7. The system of claim 1, wherein the stage-two device is configured to transmit the user instructions to the stage-one sensor device, wherein the stage-one sensor device is configured to operate the plurality of sensors in accordance with the user instructions, and wherein the user instructions include one or more of an instruction to:
start sensor data collection;
stop sensor data collection;
set a data sampling rate;
initiate sensor data transfer; and
set a signal conditioning parameter.

8. The system of claim 1, wherein the stage-two device is configured to receive instructions for operating the plurality of sensors from the remote server apparatus using the second transceiver and provide the instructions to the stage-one sensor device via the first transceiver.

9. The system of claim 1, wherein the stage-one sensor device is configured to collect the sensor data from a plurality of sensors at a respective sampling rate that is adjustable for each sensor.

10. The system of claim 9, wherein the stage-one sensor device is configured to:
analyze data received from a respective sensor from the plurality of sensors; and
adjust the respective sampling rate for the respective sensor based on the analysis.

11. The system of claim 9, wherein the stage-one sensor device is configured to:
analyze data received from a first sensor from the plurality of sensors; and
collect or abstain from collecting data from a second sensor from the plurality of sensors based on the analysis.

12. The system of claim 1, wherein the stage-one sensor device is configured to perform data conditioning that comprises one or more of:
individually calibrating one or more sensors;
cross calibrating at least two sensors;
identifying a reference temperature for one or more sensors; and
compensating the sensor data based on temperature.

13. The system of claim 1, wherein the stage-two device is configured to download firmware into the memory of the stage-one sensor device, wherein the new firmware is for one or more of updating the stage-one sensor device and calibrating the stage-one sensor device.

14. The system of claim 1, wherein processing the sensor data by the stage-two device includes redacting at least a portion of the sensor data.

15. The system of claim 1, wherein processing the sensor data by the stage-two device includes determining a performance parameter based on the sensor data.

16. The system of claim 15, wherein the performance parameter includes one or more of: a maximum speed and a total distance.

17. The system of claim 15, wherein the performance parameter is displayed via a display screen of the user interface.

18. The system of claim 3, wherein the server computing apparatus is configured to transmit the action performance characteristics parameters to the stage-two device, and the stage-two device is configured to display the action performance characteristics parameters on a display screen of the user interface.

19. The system of claim 2, wherein the server computing apparatus is configured to:
perform, based on the processed sensor data, a cross-correlation between at least two sensors providing the sensor data;
generate respective parameters for calibrating the at least two sensors based on the cross-correlation; and
transmit the respective parameters for calibrating the at least two sensors to the stage-two device for delivery to the respective sensors via the stage-one sensor device.

20. The system of claim 1, wherein the stage-one sensor device comprises a plurality of sensors, wherein the plurality of sensors are attached to a respective plurality of locations of one or more of the user and the user's equipment.

21. A method comprising:
collecting sensor data from a plurality of sensors by a stage-one sensor device attached to a user during performance of sports actions, wherein the sensors are configured to obtain measurements related to motions of the user in the sport actions;
wirelessly transmitting the sensor data, by the stage-one sensor device, to a stage-two device;
processing the sensor data by the stage-two device and presenting the processed sensor data via a user interface coupled to the stage-two device;
wirelessly transmitting, by the stage-two device over a network, the processed sensor data to a server computing apparatus disposed at a location remote to the stage-one sensor device and the stage-two device, wherein the server computing apparatus is configured to time synchronize the processed sensor data from the plurality of sensors.

* * * * *